United States Patent
Smith et al.

(10) Patent No.: US 7,096,867 B2
(45) Date of Patent: *Aug. 29, 2006

(54) NASAL MASKS

(75) Inventors: Nicholas Charles Alan Smith, Hamilton (NZ); Alastair Edwin McAuley, Auckland (NZ); Chris Earl Nightingale, Tel Aviv (IL); Ivan Milivojevic, Auckland (NZ); Lewis George Gradon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 10/495,070

(22) PCT Filed: Oct. 25, 2002

(86) PCT No.: PCT/NZ02/00227

§ 371 (c)(1),
(2), (4) Date: Sep. 17, 2004

(87) PCT Pub. No.: WO03/039637

PCT Pub. Date: May 15, 2003

(65) Prior Publication Data

US 2005/0028820 A1    Feb. 10, 2005

(30) Foreign Application Priority Data

Nov. 5, 2001   (NZ) .................................. 515257

(51) Int. Cl.
*A62B 18/08* (2006.01)

(52) U.S. Cl. ............................. 128/207.11; 128/206.27

(58) Field of Classification Search ........... 128/206.13, 128/206.27, 207.11, 207.17, 206.12, 206.18, 128/206.21, 206.28, 207.13, DIG. 26

See application file for complete search history.

(56) References Cited

U.S. PATENT DOCUMENTS 1,081,745 A   12/1913   Johnston et al.

(Continued)

FOREIGN PATENT DOCUMENTS

AU   648051   1/1952

(Continued)

*Primary Examiner*—Henry Bennett
*Assistant Examiner*—Shumaya B Ali
(74) *Attorney, Agent, or Firm*—Trexler, Bushnell, Giangiorgi, Blackstone & Marr, Ltd.

(57) ABSTRACT

The present invention is related to patient interfaces, such as nasal masks (2), particularly though not solely for use in providing continuous positive airway pressure therapy or positive pressure ventilation to patients suffering from obstructive sleep apnoea. In a first form the invention is a patient interface that has securement means (601) releasably attaching the interface to headstraps wherein the securement means (601) is slidably engaged with the patient interface. In a second form of the invention the mask headgear is formed of a plurality of straps (701, 702) where at least one of the plurality of straps is slidably engaged with another of the plurality of straps. In a further form the patient interface may be provided with vertically adjustable engaging means (802) that engage the patient interface with the headgear straps.

18 Claims, 9 Drawing Sheets

U.S. PATENT DOCUMENTS

| | | | |
|---|---|---|---|
| 1,356,708 A | 10/1920 | Goodyear | |
| 1,443,820 A | 1/1923 | Hudson | |
| 2,383,649 A | 8/1945 | Heidbrink | |
| 2,414,405 A | 1/1947 | Bierman et al. | |
| 2,444,417 A | 7/1948 | Bierman | |
| 2,675,803 A | 4/1954 | Kaslow | |
| 2,765,792 A | 10/1956 | Nichols | |
| 2,837,090 A | 6/1958 | Bloom et al. | |
| 3,013,556 A | 12/1961 | Galleher, Jr. | |
| 3,065,747 A * | 11/1962 | Forkel | 128/201.24 |
| 3,079,917 A | 3/1963 | Pate | |
| 3,513,844 A | 5/1970 | Smith | |
| 3,643,660 A | 2/1972 | Hudson et al. | |
| 3,792,702 A | 2/1974 | Delest | |
| 3,910,269 A * | 10/1975 | Ansite et al. | 128/201.24 |
| 3,987,798 A | 10/1976 | McGinnis | |
| 4,002,167 A | 1/1977 | Rambosek | |
| 4,106,505 A | 8/1978 | Salter et al. | |
| 4,120,300 A | 10/1978 | Tiep | |
| 4,151,843 A | 5/1979 | Brekke et al. | |
| 4,235,229 A | 11/1980 | Ranford et al. | |
| 4,414,973 A * | 11/1983 | Matheson et al. | 128/206.15 |
| 4,459,983 A | 7/1984 | Beyreuther et al. | |
| 4,641,647 A | 2/1987 | Behan | |
| 4,732,147 A | 3/1988 | Fuller | |
| 4,739,755 A * | 4/1988 | White et al. | 128/206.12 |
| 4,774,946 A | 10/1988 | Ackerman et al. | |
| 4,823,789 A | 4/1989 | Beisang, III | |
| 4,907,584 A | 3/1990 | McGinnis | |
| 5,003,632 A * | 4/1991 | Claude | 2/422 |
| 5,038,776 A * | 8/1991 | Harrison et al. | 128/207.11 |
| 5,042,477 A | 8/1991 | Lewis | |
| 5,042,478 A | 8/1991 | Kopala et al. | |
| 5,069,206 A | 12/1991 | Crosbie | |
| 5,074,295 A | 12/1991 | Willis | |
| 5,097,827 A | 3/1992 | Izumi | |
| 5,117,818 A | 6/1992 | Palfy | |
| 5,123,410 A | 6/1992 | Greene et al. | |
| 5,146,913 A | 9/1992 | Khorsandian et al. | |
| 5,156,641 A | 10/1992 | White | |
| 5,181,507 A | 1/1993 | Michel et al. | |
| 5,193,532 A | 3/1993 | Moa et al. | |
| 5,237,986 A | 8/1993 | Seppala et al. | |
| 5,243,971 A | 9/1993 | Sullivan et al. | |
| 5,251,616 A | 10/1993 | Desch | |
| 5,271,391 A | 12/1993 | Graves | |
| 5,282,463 A | 2/1994 | Hammersley | |
| 5,383,451 A * | 1/1995 | DeIulio | 128/207.17 |
| 5,477,852 A | 12/1995 | Landis et al. | |
| 5,513,635 A | 5/1996 | Bedi | |
| 5,533,506 A | 7/1996 | Wood | |
| 5,537,997 A | 7/1996 | Mechlenburg et al. | |
| 5,542,128 A | 8/1996 | Lomas | |
| 5,570,689 A | 11/1996 | Starr et al. | |
| 5,653,228 A | 8/1997 | Byrd | |
| 5,662,101 A | 9/1997 | Ogden et al. | |
| 5,682,881 A | 11/1997 | Winthrop et al. | |
| 5,687,715 A | 11/1997 | Landis et al. | |
| 5,735,272 A | 4/1998 | Dillon et al. | |
| 5,752,510 A | 5/1998 | Goldstein | |
| 5,832,918 A | 11/1998 | Pantino | |
| 5,921,239 A | 7/1999 | McCall et al. | |
| 5,975,077 A | 11/1999 | Hofstetter et al. | |
| 5,975,079 A | 11/1999 | Hellings | |
| 6,019,101 A | 2/2000 | Cotner et al. | |
| 6,044,844 A | 4/2000 | Kwok et al. | |
| 6,047,699 A | 4/2000 | Ryatt et al. | |
| 6,192,886 B1 | 2/2001 | Rudolph | |
| 6,321,391 B1 * | 11/2001 | Basso | 2/452 |
| 6,338,342 B1 | 1/2002 | Fecteau et al. | |
| 6,374,826 B1 | 4/2002 | Gunaratnam et al. | |
| 6,457,473 B1 | 10/2002 | Brostrom et al. | |
| 6,470,886 B1 | 10/2002 | Jestrabek-Hart | |
| 6,494,207 B1 | 12/2002 | Kwok | |
| 6,520,182 B1 | 2/2003 | Gunaratnam | |
| 6,536,435 B1 | 3/2003 | Fecteau et al. | |
| 6,536,436 B1 | 3/2003 | McGlothen | |
| 6,591,837 B1 | 7/2003 | Byram | |
| 6,612,309 B1 | 9/2003 | Ancona | |
| 6,615,834 B1 | 9/2003 | Gradon et al. | |
| 6,691,708 B1 | 2/2004 | Kwok et al. | |
| 6,701,926 B1 | 3/2004 | Olsen et al. | |
| 6,715,490 B1 | 4/2004 | Byram | |
| 6,796,308 B1 * | 9/2004 | Gunaratnam et al. | 128/206.24 |
| 6,823,869 B1 * | 11/2004 | Raje et al. | 128/206.24 |
| 6,840,238 B1 * | 1/2005 | Van Hegelsom | 128/201.22 |
| 2002/0005201 A1 | 1/2002 | Gradon | |
| 2003/0000533 A1 | 1/2003 | Olsen et al. | |
| 2003/0111080 A1 * | 6/2003 | Olsen et al. | 128/207.11 |
| 2004/0112377 A1 * | 6/2004 | Amarasinghe et al. | 128/201.22 |
| 2004/0244804 A1 * | 12/2004 | Olsen et al. | 128/207.18 |
| 2005/0056286 A1 * | 3/2005 | Huddart et al. | 128/206.21 |

FOREIGN PATENT DOCUMENTS

| | | |
|---|---|---|
| EP | 1084727 | 3/2001 |
| EP | 1163924 | 12/2001 |
| WO | WO 8703704 | 6/1987 |
| WO | WO 9848876 | 11/1998 |
| WO | WO 0189381 | 11/2001 |

* cited by examiner

NASAL MASKS

BACKGROUND OF THE INVENTION

1. Field of the Invention

This invention relates to patient interfaces, particularly though not solely for use in providing Continuous Positive Airway Pressure (CPAP) therapy or positive pressure ventilation to patients suffering from obstructive sleep apnoea (OSA).

2. Summary of the Prior Art

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (ie. aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives will not be achieved, or will be achieved with great difficulty and considerable user discomfort.

In common with prior art designs, is an inability to seal effectively when the user's face becomes distorted. For example, as shown in the prior art mask of FIG. 1 when the user 100 is sleeping on his or her side, one side 101 of the headgear tends to be pulled tight while the other side 102 tends to be loose. This causes the axis of the mask 103 to be twisted with respect to the axis of the head 104, due to the net torque from the headgear, resulting in leakage 105 on one side. The user 100 sleeping on his or her side may also distort the facial contours around the nasal area 106 and may lead to further leakage.

SUMMARY OF THE INVENTION

It is an object of the present invention to provide a nasal mask and headgear which goes some way to overcoming the abovementioned disadvantages in the prior art or which will at least provide the industry with a useful choice.

Accordingly in a first aspect the present invention may broadly be said to consist in a device for delivering a supply of gases to a user comprising or including:

a patient interface, which in use is in fluid communication with said supply of gases, securement means attached to or around the head of said user, and engaging means adapted to slidingly engage said securement means with said patient interface, wherein said engaging means comprises or includes an attachment portion able to be engaged with said securement means and the engagement between said securement means and said engaging means is caused by the releasable engagement of a protrusion, located on one of said attachment portion and said securement means, into a complementary shaped aperture located on one of said member and said securement means.

In a second aspect the present invention consists in continuous positive airways pressure system for delivering gases to a user comprising or including a pressurised source of gases, transport means in fluid communication with said pressurised source adapted to convey said gases, and a nasal mask in fluid communication with said transport means, in use, delivering said gases to said user, said nasal mask comprising or including:

a body portion having an inlet, in use said inlet receiving a supply of gases, sealing means engaged with said body portion, and adapted to seal against the facial contours of said user, and engaging means adapted to in use provide a sliding engagement with a means of securement to a user, and a compressive force on said sealing means to ensure said supply of gases is delivered to a user without significant leakage, wherein said engaging means comprises or includes an attachment portion able to be engaged with said securement means and the engagement between said securement means and said engaging means is caused by the releasable engagement of a protrusion, located on one of said attachment portion and said securement means, into a complementary shaped aperture located on one of said member and said securement means.

In a third aspect the present invention consists in a device for delivering a supply of gases to a user comprising or including:

a patient interface, which in use is in fluid communication with said supply of gases, securement means attached to or around the head of said user, and engaging means adapted to slidingly engage said securement means with said patient interface, restraining means on said patient interface to restrain said engaging means at least in one dimension on said patient interface, but allowing said engaging means to slide within said restraining means in at least one other dimension, said restraining means being substantially vertically adjustable on said patient interface in either a freely moveable position or lockable in at least one vertical position.

In a fourth aspect the present invention consists in a continuous positive airways pressure system for delivering gases to a user comprising or including a pressurised source of gases, transport means in fluid communication with said pressurised source adapted to convey said gases, and a nasal mask in fluid communication with said transport means, in use, delivering said gases to said user, said nasal mask comprising or including:

a body portion having an inlet, in use said inlet receiving a supply of gases, sealing means engaged with said body portion, and adapted to seal against the facial contours of said user, and engaging means adapted to in use provides a sliding engagement with a means of securement to a user, and a compressive force on said sealing means to ensure said supply of gases is delivered to a user without significant leakage, restraining means on said body portion to restrain said engaging means at least in one dimension on said body portion, but allowing said engaging means to slide within at least one other dimension, said restraining means being substantially vertically adjustable on said body portion in either a freely moveable position or lockable in at least one vertical position.

In a fifth aspect the present invention consists in a device for delivering a supply of gases to a user comprising or including:
  a patient interface, which in use is in fluid communication with said supply of gases,
  securement means attached to or around the head of said user, and
  engaging means adapted to engage said securement means with said patient interface,
  wherein said securement means comprises or includes a plurality of straps that are fastened around the head of said user in order to secure said patient interface to said users' face, and at least one of said plurality of straps is slidably engaged with another of said plurality of straps.

In a sixth aspect the present invention consists in a continuous positive airways pressure system for delivering gases to a user comprising or including a pressurised source of gases, transport means in fluid communication with said pressurised source adapted to convey said gases, and a nasal mask in fluid communication with said transport means in use delivering said gases to said user, said nasal mask comprising or including:
  a body portion having an inlet, in use said inlet receiving a supply of gases,
  sealing means engaged with said body portion, and adapted to seal against the facial contours of said user, and
  engaging means adapted to in use provide a sliding engagement with a means of securement to a user, and a compressive force on said sealing means to ensure said supply of gases is delivered to a user without significant leakage,
  wherein said means of securement comprises or includes a plurality of straps, which are fastened around the head of said user in order to secure said patient interface to said users' face, and at least one of said plurality of straps is slidably engaged with another of said plurality of straps.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the field of nasal masks for use in positive pressure ventilation. In particular a nasal mask is described which is more comfortable for the user to wear and reduces the side leakage as compared with masks of the prior art. It will be appreciated that the nasal mask as described in the preferred embodiment of the present invention can be used in respiratory care generally or with a ventilator but will now be described below with reference to use in a humidified positive pressure ventilation system.

Figure 2:
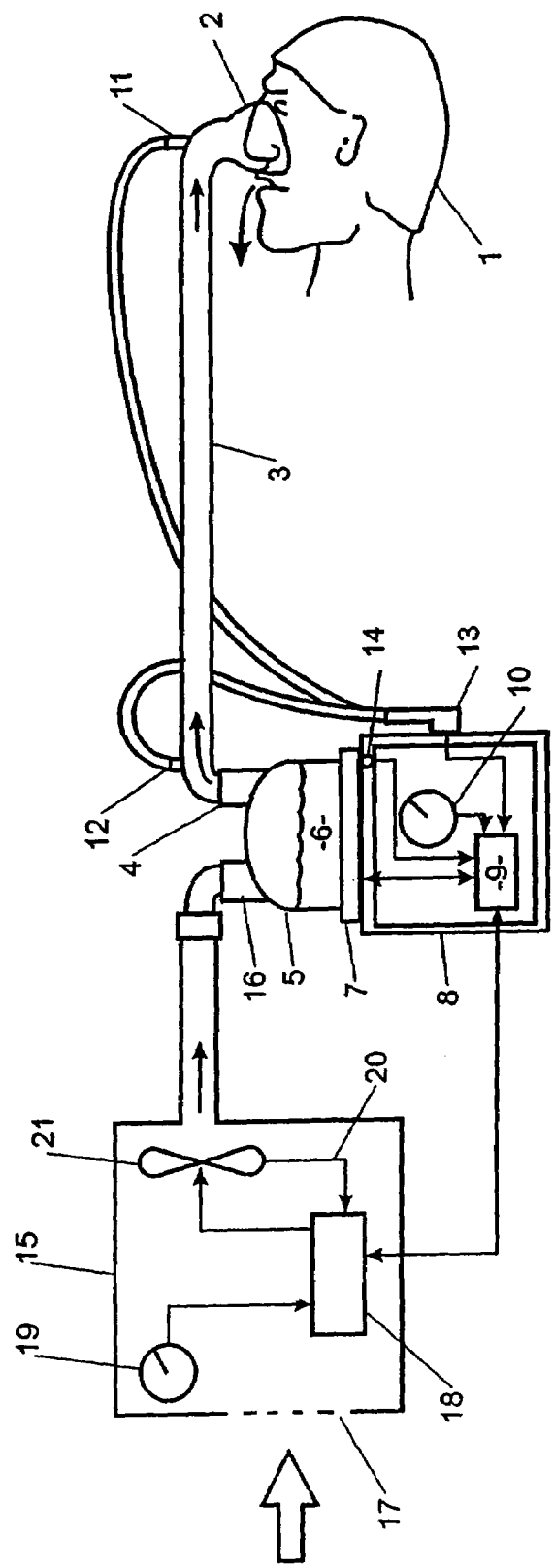
FIG. 2 is a block diagram of a humidified positive pressure ventilation system as might be used in conjunction with the present invention.

With reference to FIG. 2 a humidified positive pressure ventilation system is shown in which a patient 1 is receiving humidified and pressurised gases through a nasal mask 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 3.

Blower 15 is provided with variable pressure regulating means or variable speed fan 21 which draws air or other gases through blower inlet 17. The speed of variable speed fan 21 is controlled by electronic controller 18 (or alternatively the function of controller 18 could be carried out by controller 9) in response to inputs from controller 9 and a user set predetermined required value (preset value) of pressure or fan speed via dial 19.

Nasal Mask

Figure 3:
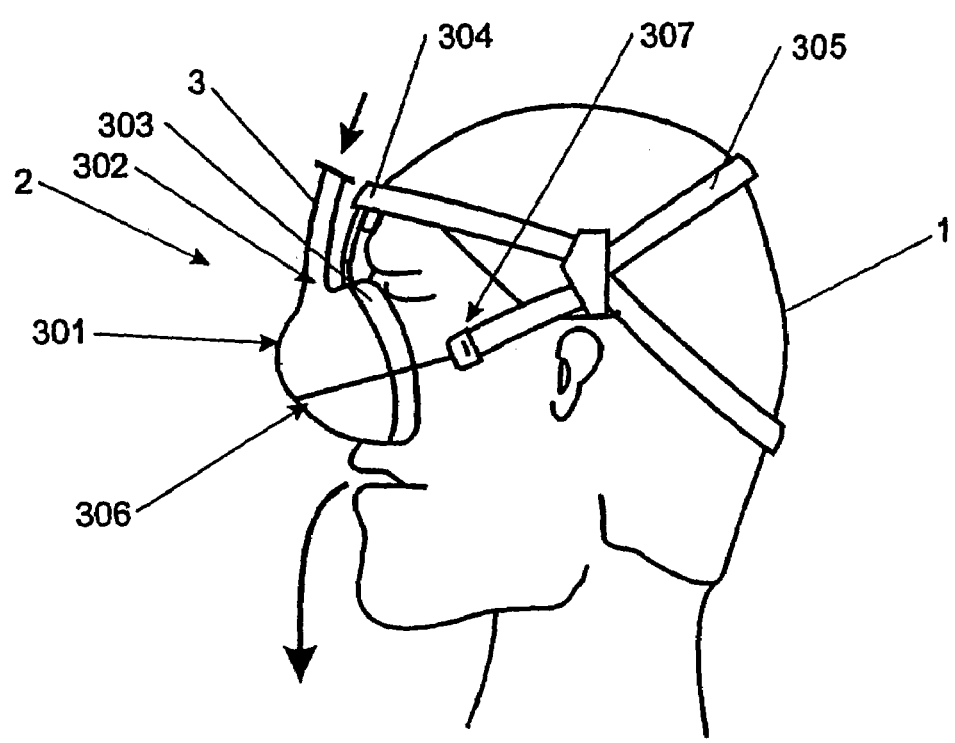
FIG. 3 is an illustration of a prior art nasal mask that may be used with the headgear and glider straps of one of the preferred embodiment of the present invention.

A nasal mask that may be used with the improvements to the securement means (headgear) and engagement means (glider straps) of the present invention is shown in FIG. 3. The patient interface or mask includes a hollow body 301 with an inlet 302 connected to the inspiratory conduit 3. The mask 2 is positioned around the nose of the user 1 with the headgear 305 secured around the back of the head of the patient 1. The restraining force from the headgear 305 on the hollow body 301 and the forehead rest 304 ensures enough compressive force on the mask cushion 303, to provide an effective seal against the patient's face.

The hollow body 301 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Headgear

Figure 4:
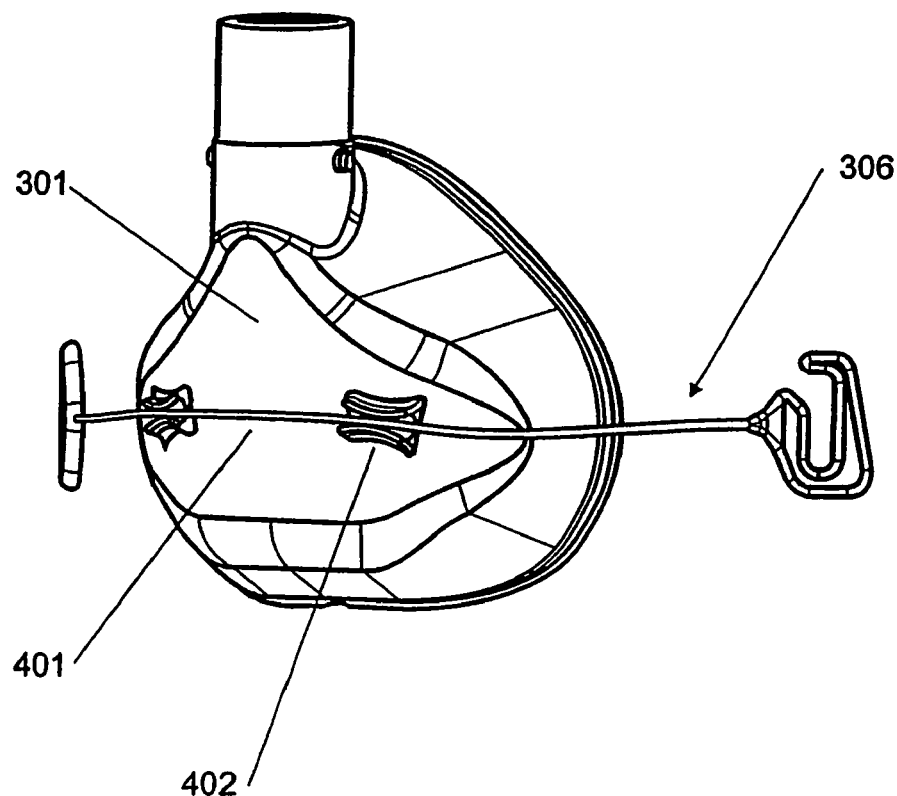
FIG. 4 is a perspective view of a prior art nasal mask illustrating a sliding strap clipped in place on the mask.

Referring now to FIGS. 3 and 4, the headgear 305 of a prior art device is shown that may be connected to the hollow body 301. Rather than traditional fixed or adjustable attachments the present invention utilises a sliding engagement means (glider strap) between the headgear 305 and the hollow body 301. This is achieved with a sliding member 306, running through harnessing means (only one 307 is shown in FIG. 3) located on either side of the headgear 305 and over the top of the hollow body 301. The sliding member 306 is reciprocally engaged with guides 401, 402 mounted on the top surface of the hollow body 301. The guides constrain the member 306 but allow it to slide sideways, meaning the headgear 305 can move laterally, independently of the hollow body 306. Thus as a user's face is contorted during various sleeping positions the headgear is able to move with the changes in position while the mask is left in the correct position on the nose of the user and an effective seal is maintained.

To further ensure user comfort and effective pressure on the mask cushion 303, the headgear 305 may be constructed either using two straps running around the back of the user's head as shown in FIG. 3 or with a partial skull cap or any other configurations as are known in the art. In this case the straps or partial skull cap would be constructed using neoprene but may also be constructed using any material as is known in the art which will be comfortable for the user.

Figure 5:
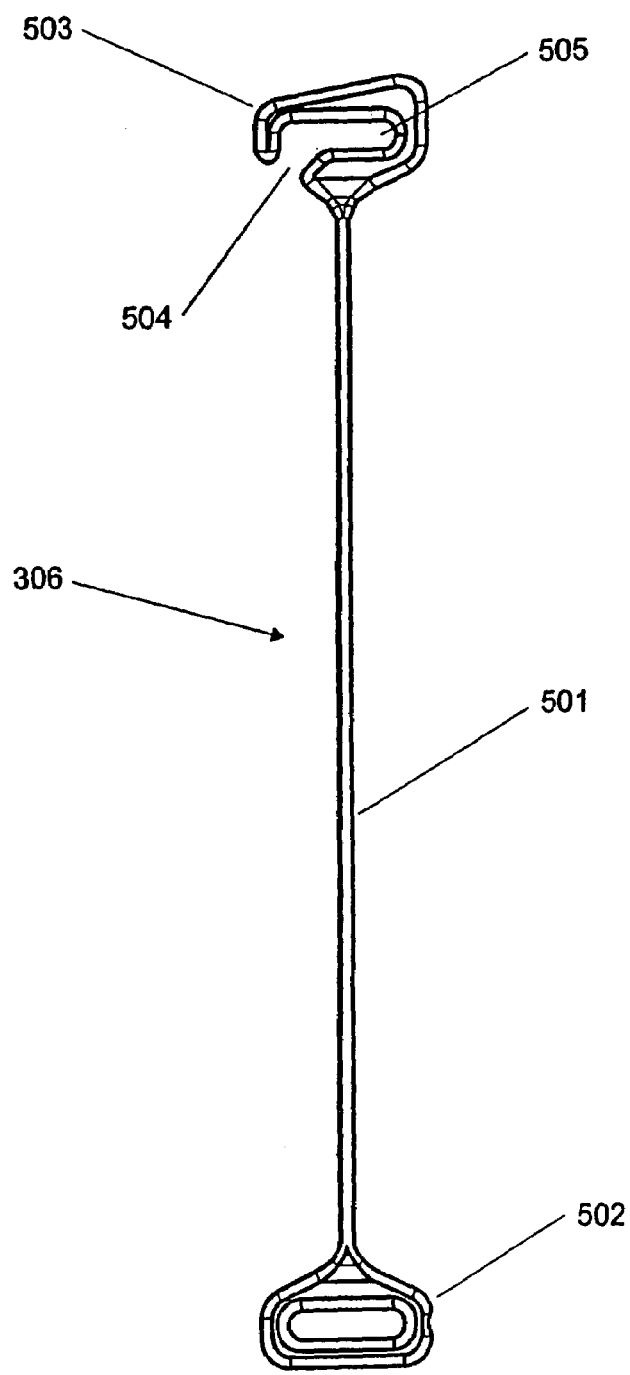
FIG. 5 is a side view of the sliding strap of the prior art.

The sliding member 306 of the prior art, shown in FIG. 5 in isolation, is constructed of polyacetal (Delrin 500P NC010) using injection moulding techniques to give a polished finish. This material, similar to other nylon based derivatives, with its polished finish has a particularly low friction coefficient, and therefore slides with respect to the hollow body 301 with very little resistance.

As shown in FIG. 4, the hollow body 301 has engaging guides 401, 402, wherein use the sliding member 306 snaps into place into the engaging guides (401, 402) and can only be removed therefrom using a substantial force. This means that with any normal use the sliding member 306 will stay retained within the engaging clips 401, 402.

As shown in FIG. 5 the sliding strap includes a midsection 501 intended to reciprocate with the engaging guides, terminated at each end by loops 502, 503 which attach to the headgear. The first loop 502 is a full loop through which the headgear 305 is permanently attached with for example, a velcro strap. The loop 503 at the other end, is only a partial loop 504 designed so that a strap or loop from the headgear 305 can be easily slipped in or out of the open section 505 to allow easy removal and attachment of the mask.

Sliding Member Attachment Portion

Figure 6:
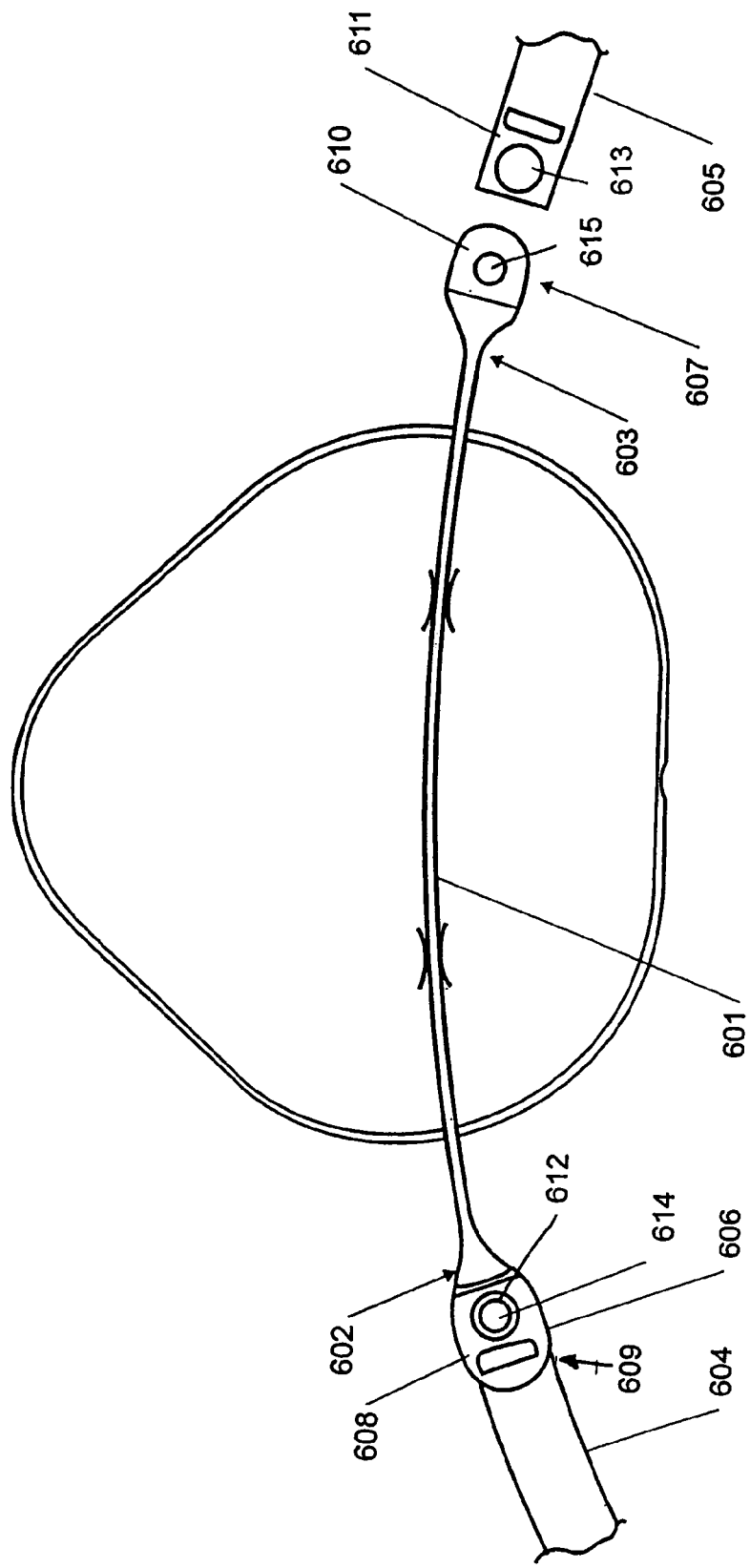
FIG. 6 is a front view of a sliding strap with clipping attachment means for use with a nasal mask of the present invention.

The nasal mask of the present invention has a sliding member similar to that described above. As shown in FIG. 6, the ends 602, 603 of the sliding member 601 are attached to the headgear straps 604, 605 by way of engaging means 606, 607. The engaging means 606, 607 comprise two parts. Firstly, attachment portions are integrally formed on the each end 602, 603 of the sliding member 601. Secondly, complimentary portions (to the attachment portions) are either integrally formed or attached to the ends of the headgear straps 604, 605. Each of the attachment and complementary portions are releasably attached to one another. Each attachment portion is a substantially square section 608, 610 each having an aperture 614, 615. The ends of the headgear strap 609, 611 each having a complimentary portion having a protrusion 612, 613 fittable within the aperture 614, 615 of the attachment portion 608, 610. Effectively, in use, when attaching the sliding member 601 to the headgear straps 604, 605, the protrusion 612, 613 is fitted into the aperture 614, 615 on the attachment portion, thereby maintaining a connection between the sliding member and the headgear straps.

Alternatively, the protrusions 612, 613 as described above may be located on the attachment portions of the sliding member 601 and the apertures 614, 615 on the ends of the headgear straps.

In FIG. 6 the protrusions 612, 613 is shown as being larger than the apertures 614, 615. This is because the material making up the attachment portions and the end of the headgear straps is a deformable material, preferably of the plastics type, that allows for the large protrusion to be forced through the smaller aperture. The protrusion and aperture remain engaged until an opposing force causes the protrusion to disengage or be pulled from the aperture.

Sliding Headgear Strap

Figure 1:
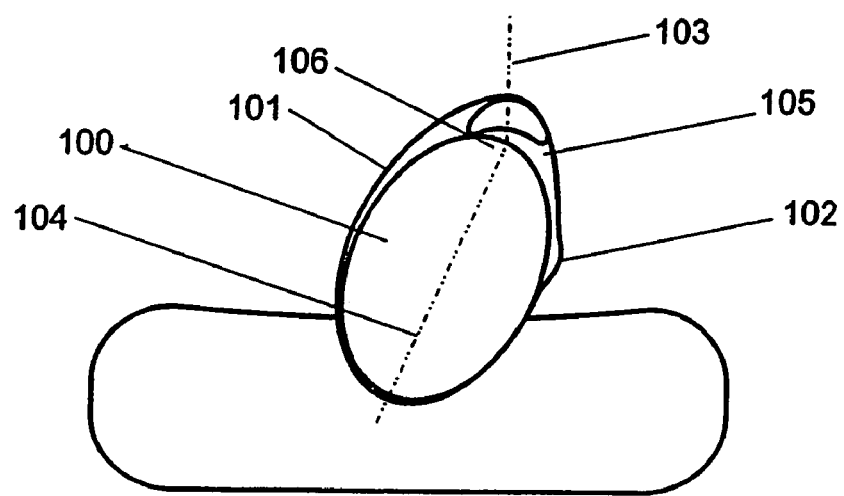
FIG. 1 is a plan view of a prior art mask illustrating side leak.
Figure 7:
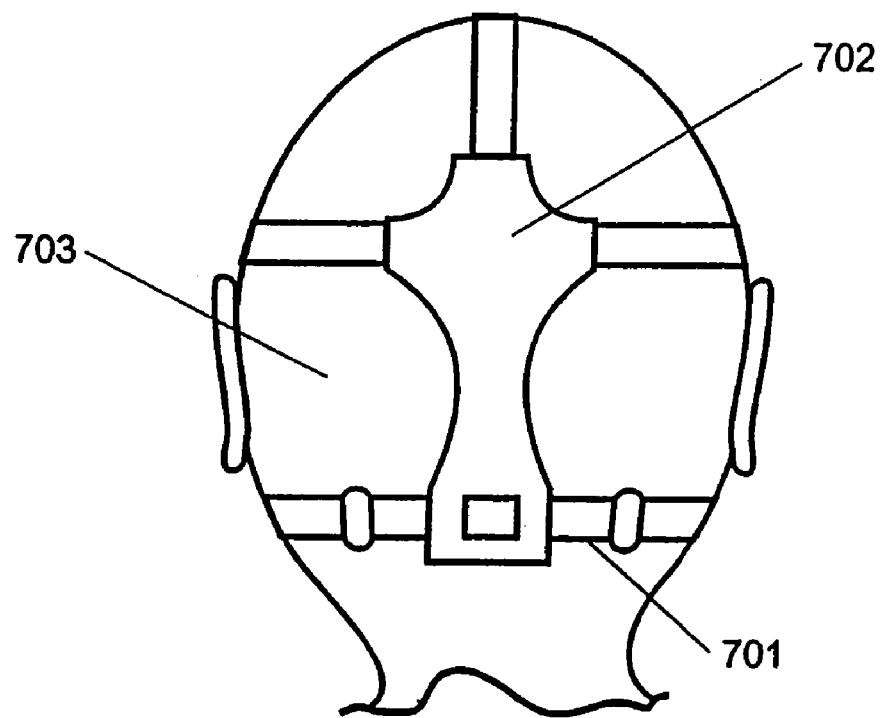
FIG. 7 is an illustration of the headgear attaching a nasal mask of the present invention to a user's head, showing a sliding strap in the back sections of the headgear.

The nasal mask of the present invention in an alternative form may also be provided with headgear utilising a sliding strap. FIG. 7 shows a sliding strap 701 that is located at the back of the user's head. When the user 703 turns their head, the circumferential distance from the nose to the back of the head changes. In prior art devices this movement produces unequal tension in the straps of the restraining headgear and therefore pulls the nasal mask in the direction of increased tension. By allowing the strap 701 to 'slide' within the rest of the headgear, in particular the skullcap portion 702, an equal tension is produced and any translation of these forces to the mask is eliminated, hence side leakage as described earlier in relation to the prior art mask of FIG. 1 is reduced.

Vertical Adjustment for Sliding Member

Figure 8:
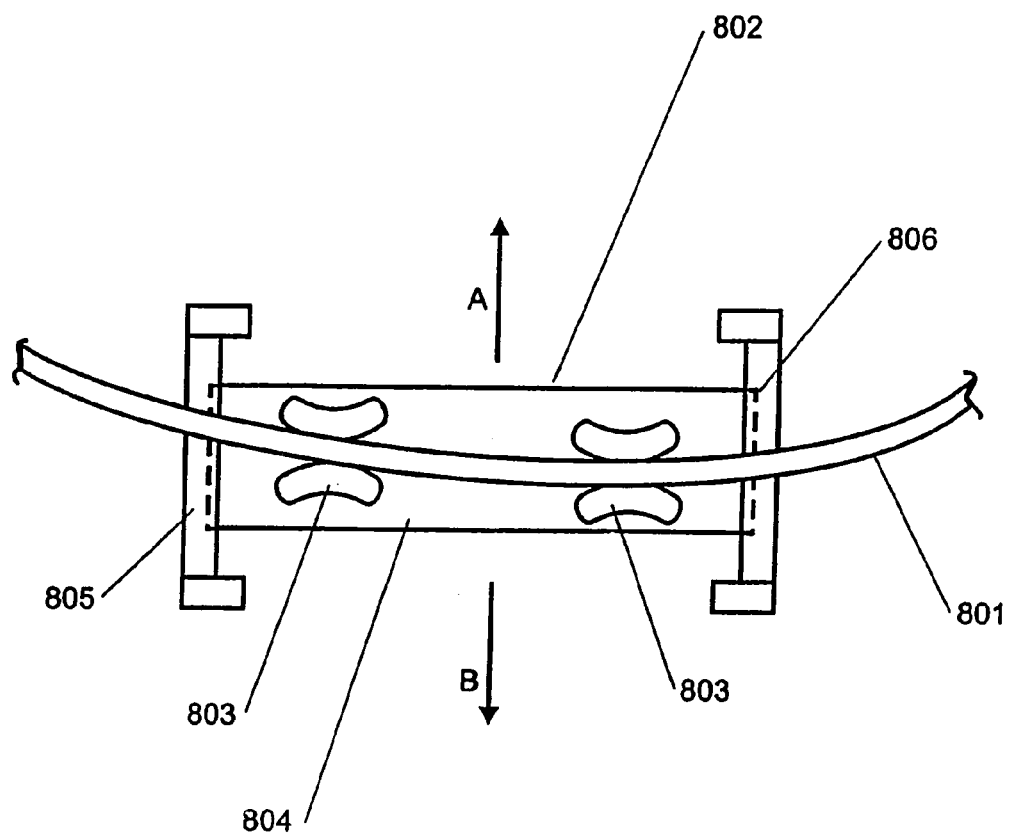
FIG. 8 is a front view of an alternative form of the sliding strap of the present invention.

The nasal mask of the present invention in an alternative form may also be provided with adjustment means that allows for vertical adjustment of the sliding member. Due to variations in the size of user's head of the nasal mask, the location of the restraining means (engaging guides as referred to earlier with reference to FIG. 4, which hold the sliding member on the mask) that guide the "sliding member" is not always desirable. Allowing these guides to move vertically creates a more desirable mask for the user and may assist in reducing side leakages. The vertical movement of the guides also overcomes the problems with over tightening of the headgear straps that occurs when the user tilts their head vertically. FIG. 8 shows restraining means that are vertically adjustable and which may be utilised with the sliding member of the present invention. The vertically adjustable restraining means 802 is a substantially rectangular section 804 having located thereon engaging guides 803, that the sliding member 801 is pushed into, these guides retain the member 801 but allow it to slide within the guides 803. The rectangular section 804 is located and moveable within vertical slides 805, 806. These slides 805, 806 are attached by appropriate means to the mask body (301 on FIG. 3). The rectangular section 804, guides 803 and thus sliding member 801 can therefore be moved up and down as indicated by arrows A and B. The rectangular section 804 may be freely moveable within the slides 805,806 or may be moved and locked in various vertical positions.

Alternative Sliding Member

Figure 9:
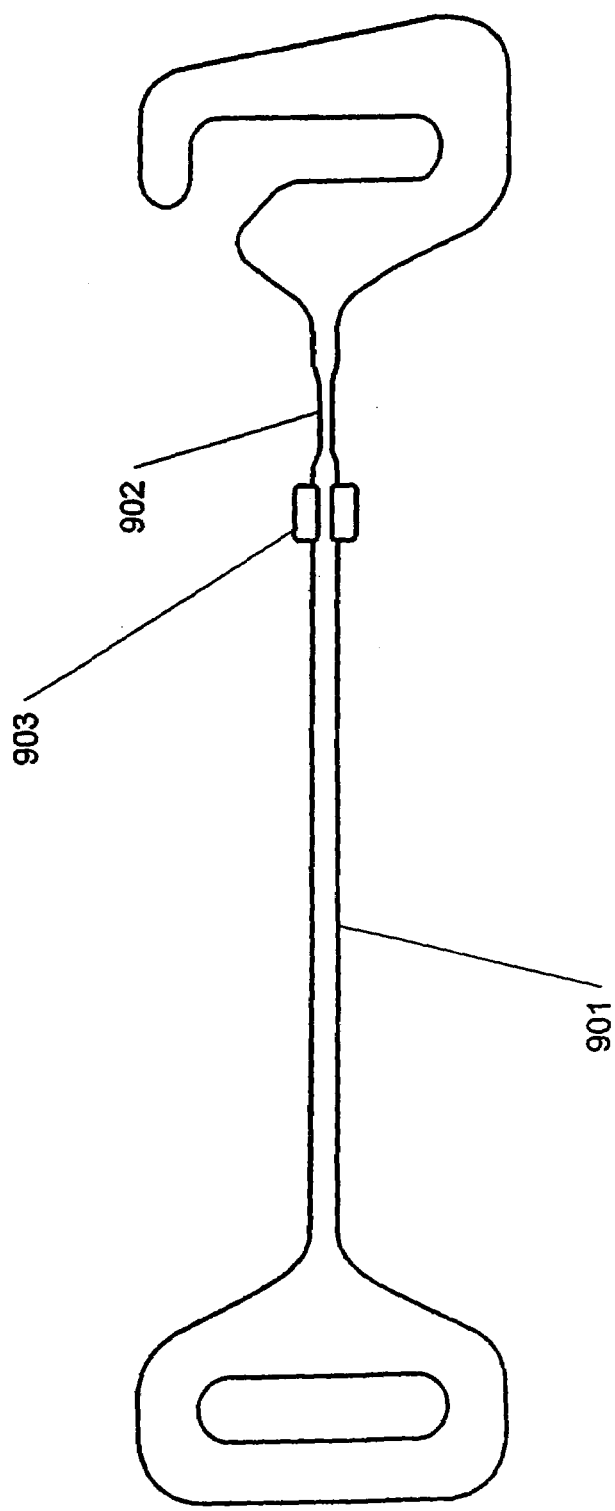
FIG. 9 shows a side views of an alternative form of the sliding strap as may be used with the nasal mask of the present invention.

The nasal mask of the present invention in an alternative form may also be provided with an alternative sliding member. A user may find it difficult to insert the sliding member as described above into the engaging guides on the mask 301. FIG. 9 illustrates an alternative sliding member 901 having a section 902 with reduced diameter at one of its ends. The reduced diameter section 902 makes it easier to insert the sliding member 901 into the engaging guides on the mask base. When a user puts on the nasal mask and attaches the sliding member to the front of the mask within the engaging guides 903, the user places the narrowed section 902 of the sliding member 901 within the engaging guides and moves the sliding member in a lateral direction into an "in use" position where the wider diameter of the sliding member resides within the guides. Thus tie larger diameter section of the sliding member 901 that remains in the engaging guides is more difficult to remove from the guides.

We claim:

1. A device for delivering a supply of gases to a user comprising or including:
    a patient interface, which in use is in fluid communication with said supply of gases,
    securement means attached to or around the head of said user, and
    engaging means adapted to slidingly engage said securement means with said patient interface,
    restraining means on said patient interface to restrain said engaging means at least in one dimension on said patient interface, but allowing said engaging means to slide within said restraining means in at least one other dimension, said restraining means being substantially vertically adjustable on said patient interface in either a freely moveable position or lockable in at least one vertical position.

2. A device for delivering gases to a user according to claim 1 wherein said engaging means is an elongate member.

3. A device for delivery gases to a user according to any one of claims 1 or 2 wherein said patient interface is a nasal mask.

4. A device for delivering gases to a user according to claim 1 wherein said elongate member has a section along it's length that is narrower in diameter than the rest of said elongate members length, said narrower section being easily fittable into said at least one restraining means, to allow for the ease of fitting or removal of said member within said at least one restraining means.

5. A continuous positive airways pressure system for delivering gases to a user comprising or including a pressurised source of gases, transport means in fluid communication with said pressurised source adapted to convey said gases, and a nasal mask in fluid communication with said transport means, in use, delivering said gases to said user, said nasal mask comprising or including:
    a body portion having an inlet, in use said inlet receiving a supply of gases,
    sealing means engaged with said body portion, and adapted to seal against the facial contours of said user, and
    engaging means adapted to in use provide a sliding engagement with a means of securement to a user, and a compressive force on said sealing means to ensure said supply of gases is delivered to a user without significant leakage,
    restraining means on said body portion to restrain said engaging means at least in one dimension on said body portion, but allowing said engaging means to slide within at least one other dimension, said restraining means being substantially vertically adjustable on said body portion in either a freely moveable position or lockable in at least one vertical position.

6. A device for delivering gases to a user according to claim 5 wherein said engaging means is an elongate member.

7. A device for delivering gases to a user according to claim 6 wherein said elongate member has a section along it's length that is narrower in diameter than the rest of said elongate members length, said narrower section being easily fittable into said at least one restraining means, to allow for the ease of fitting or removal of said member within said at least one restraining means.

8. A device for delivering a supply of gases to a user comprising or including:
    a patient interface, which in use is in fluid communication with said supply of gases,
    securement means attached to or around the head of said user, and
    engaging means adapted to engage said securement means with said patient interface,
    wherein said securement means comprises or includes a plurality of straps that are fastened around the head of said user in order to secure said patient interface to said user's face, and at least one of said plurality of straps is slidably engaged with another of said plurality of straps.

9. A device for delivering a supply of gases to a user according to claim 8 wherein said patient interface is a nasal mask.

10. A device for delivering a supply of gases to a user according to claim 9 wherein said nasal mask comprises or includes a body portion having an inlet receiving said supply of gases, and sealing means attached to or integrated with said body portion said sealing means adapted to seal against the facial contours of said user.

11. A device for delivering a supply of gases to a user according to claim 10 wherein said engaging means slidingly engages said securement means with said nasal mask and is adapted to allow said securement means substantial movement with respect to said nasal mask, while still providing compressive force on said sealing means to ensure said supply of gases is delivered to said user without significant leakage.

12. A device for delivering a supply of gases to a user according to claim 8 wherein said engaging means further comprises or includes an elongate member and at least one restraining means on said patient interface, in use said member is restrained in at least one dimension by said restraining means, but allowing said member to slide easily within at least one other dimension, said restraining means adapted to in use easily disengage with said member.

13. A device for delivering a supply of gases to a user according to claim 12 wherein said restraining means is vertically adjustable upon said body portion in either a freely movable manner or lockable in at least one vertical position.

14. A device for delivering a supply of gases according to claim 8 wherein said elongate member has a section along it's length that is narrower in diameter than the rest of said elongate members length, said narrower section being easily fittable into said at least one restraining means to allow for the ease of fitting or removal of said member within said at least one restraining means.

15. A continuous positive airways pressure system for delivering gases to a user comprising or including a pressurised source of gases, transport means in fluid communication with said pressurised source adapted to convey said gases, and a nasal mask in fluid communication with said transport means in use delivering said gases to said user, said nasal mask comprising or including:
   a body portion having a inlet, in use said inlet receiving a supply of gases,
   sealing means engaged with said body portion, and adapted to seal against the facial contours of said user, and
   engaging means adapted to in use provide a sliding engagement with a means of securement to a user, and a compressive force on said sealing means to ensure said supply of gases is delivered to a user without significant leakage, wherein said means of securement comprises or includes a plurality of straps, that are fastened around the head of said user in order to secure said patient interface to said user's face, and at least one of said plurality of straps is slidably engaged with another of said plurality of straps.

16. A continuous positive airways pressure system for delivering gases to a user according to claim 15 wherein said engaging means comprises or includes an elongate member and at least one restraining means on said body portion, in use said member is restrained in at least one dimension by said restraining means, but allowing said member to slide easily within at least one other dimension, and providing a compressive force on said sealing means to avoid any significant leakage, said restraining means adapted to in use easily disengage with said member.

17. A continuous positive airways pressure system for delivering gases to a user according to claim 16 wherein said restraining means is vertically adjustable upon said body portion in either a freely movable manner or lockable in at least one vertical position.

18. A continuous positive airways pressure system for delivering gases to a user according to any one of claims 16 or 17 wherein said elongate member has a section along it's length that is narrower in diameter than the rest of said elongate members length, said narrower section being easily fittable into said at least one restraining means, to allow for the ease of fitting or removal of said member within said at least one restraining means.

* * * * *